(12) United States Patent
Brenneman

(10) Patent No.: US 8,504,131 B2
(45) Date of Patent: *Aug. 6, 2013

(54) TRANSDERMAL ANALYTE SENSOR ASSEMBLY AND METHODS OF USING THE SAME

(75) Inventor: Allen J. Brenneman, Goshen, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/547,890

(22) Filed: Jul. 12, 2012

(65) Prior Publication Data

US 2012/0273370 A1    Nov. 1, 2012

Related U.S. Application Data

(63) Continuation of application No. 12/086,238, filed as application No. PCT/US2006/047803 on Dec. 14, 2006, now Pat. No. 8,271,064.

(60) Provisional application No. 60/751,238, filed on Dec. 16, 2005.

(51) Int. Cl.
*A61B 5/00* (2006.01)
*A61B 5/05* (2006.01)

(52) U.S. Cl.
USPC ........... 600/345; 600/309; 600/347; 600/364; 600/365; 600/366

(58) Field of Classification Search
None
See application file for complete search history.

(56) References Cited

U.S. PATENT DOCUMENTS

| | | | |
|---|---|---|---|
| 6,144,869 A | 11/2000 | Berner et al. | |
| 6,341,232 B1 | 1/2002 | Conn et al. | |
| 6,356,776 B1 | 3/2002 | Berner et al. | |
| 6,503,198 B1 | 1/2003 | Aronowtiz et al. | |
| 6,816,742 B2 | 11/2004 | Kim et al. | |
| 6,999,810 B2 | 2/2006 | Berner et al. | |
| 7,024,236 B2 | 4/2006 | Ford et al. | |
| 7,577,469 B1 | 8/2009 | Aronowitz et al. | |
| 7,860,544 B2 | 12/2010 | Say et al. | |
| 8,032,197 B2 | 10/2011 | Rebec | |
| 8,271,064 B2 * | 9/2012 | Brenneman | 600/345 |
| 8,414,489 B2 * | 4/2013 | Shah et al. | 600/365 |
| 2002/0053637 A1 | 5/2002 | Conn et al. | 250/281 |
| 2002/0155425 A1 | 10/2002 | Han et al. | |
| 2003/0100846 A1 | 5/2003 | Custer et al. | 600/573 |
| 2003/0113827 A1 | 6/2003 | Burkoth | 435/14 |
| 2004/0009100 A1 | 1/2004 | Simons et al. | |
| 2005/0153428 A1 | 7/2005 | Matsumoto | |
| 2006/0195029 A1 | 8/2006 | Shults et al. | |
| 2009/0221892 A1 | 9/2009 | Brenneman et al. | |
| 2009/0312614 A1 | 12/2009 | Brenneman | |
| 2010/0292557 A1 | 11/2010 | Pesach et al. | |
| 2012/0022354 A1 | 1/2012 | Beyer et al. | |
| 2012/0071737 A1 * | 3/2012 | Landini et al. | 600/309 |
| 2012/0116195 A1 * | 5/2012 | Chaum et al. | 600/345 |
| 2012/0252046 A1 * | 10/2012 | Fei et al. | 435/14 |
| 2012/0258467 A1 * | 10/2012 | Chinnayelka et al. | 435/7.1 |
| 2012/0273370 A1 * | 11/2012 | Brenneman | 205/792 |

FOREIGN PATENT DOCUMENTS

| | | |
|---|---|---|
| CN | 1152712 A | 6/1997 |
| EP | 0876501 B1 | 4/2001 |
| JP | 4-227235 A | 8/1992 |
| WO | WO 96/00110 | 1/1996 |
| WO | WO 00/24455 A1 | 5/2000 |

OTHER PUBLICATIONS

European Search Report for Application No. 10 17 0418 dated Nov. 29, 2010 (4 pages).
Ferrante do Amaral et al, Meidcal Engineering and Physics, 2008, 30:541-549.
International Search Report corresponding to International Patent Application No. PCT/US2006/047803, European Patent Office, dated Jul. 25, 2007, 4 pages.
Oliver et al., Diabetic Medicine, 2009, 26:197-210.
Qing-de et al., Chinese Journal Analytical Chemistry, Nov. 2009, 37/11:1566-1571.
Sieg et al, Diabetes Technology and Therapeutics, 2005, 7/1:174-179.
Tierney et al, Clinical Chemistry, 1999, 45/9:1681-83.
Written Opinion corresponding to International Patent Application No. PCT/US2006/047803, European Patent Office, dated Jul. 25, 2007, 5 pages.

* cited by examiner

*Primary Examiner* — Nita M Minnifield
(74) *Attorney, Agent, or Firm* — Nixon Peabody LLP

(57) ABSTRACT

A transdermal test sensor assembly adapted to determine an analyte concentration of a fluid sample is disclosed. The assembly comprises a sensor support including at least one reservoir adapted to hold a liquid. The assembly further comprises a test sensor being coupled to the sensor support. The test sensor forms at least one aperture therein. At least a portion of the at least one aperture is adjacent to the at least one reservoir. The assembly further comprises a hydrogel composition positioned on the test sensor. The hydrogel composition is linked to the at least one reservoir via the at least one aperture.

20 Claims, 2 Drawing Sheets

TRANSDERMAL ANALYTE SENSOR ASSEMBLY AND METHODS OF USING THE SAME

CLAIM OF PRIORITY AND CROSS-REFERENCE TO RELATED APPLICATIONS

This application is a Continuation of U.S. patent application No. 12/086,238, now U.S. Pat. No. 8,271,064 B2, which was filed on Jun. 9, 2008, as a U.S. National Phase of International Application No. PCT/US2006/047803, which was filed on Dec. 14, 2006, and claims the benefit of and priority to U.S. Provisional Patent Application No. 60/751,238, which was filed on Dec. 16, 2005, all of which are incorporated herein by reference in their respective entireties.

TECHNICAL FIELD

The present invention relates generally to a transdermal test sensor assembly. More particularly, the invention relates to a transdermal test sensor assembly adapted to assist in determining a concentration of at least one analyte, where the test sensor assembly has hydrating features.

BACKGROUND

The quantitative determination of analytes in body fluids is of great importance in the diagnoses and maintenance of certain physiological abnormalities. For example, lactate, cholesterol, and bilirubin should be monitored in certain individuals. In particular, determining glucose in body fluids is important to diabetic individuals who must frequently check the glucose level in their body fluids to regulate the glucose intake in their diets. The results of such tests may be used to determine what, if any, insulin or other medication needs to be administered. In one type of testing system, test sensors are used to test a fluid such as a sample of blood.

According to some existing techniques, a lancet may be used to pierce a user's skin to draw fluid (e.g., blood) from the user. This fluid is then used with an instrument or meter to determine an analyte (e.g., glucose) concentration. Piercing a user's skin each time an analyte concentration reading is desired is an inconvenient and invasive procedure. Moreover, the procedure is undesirable because of the resulting pain and discomfort often experienced by a user.

One non-invasive method for obtaining a sample for determining an analyte concentration involves using a transdermal sample of one or more analytes found in, for example, interstitial fluid (ISF). In this method, a transdermal test sensor is placed on a user's skin. The transdermal sensor typically includes a hydrogel composition to facilitate the extraction of the analyte of interest from the ISF via the user's skin to an analyte-testing instrument or meter. The hydrogel must be sufficiently mechanically and thermally stable to provide a relatively static, reactive, and aqueous conduct between a dermal sampling site and an analyte-testing instrument.

One problem with existing transdermal test sensors relates to having a hydrogel that is sufficiently hydrated and can maintain such hydration. Inadequate hydration may be caused by exposure to the outside environment and/or the lack of a hermetic seal between the skin and the test sensor. The level of hydration of the hydrogel (e.g., solvent content) generally decreases over time. If the level of hydration of the hydrogel falls below a certain level, the hydrogel may cease to provide intimate contact between the skin and the hydrogel and/or the hydrogel and the test sensor. Such intimate contact is necessary for accurate testing results.

Thus, it would be desirable to have a transdermal test sensor that assists in addressing one or more of the above disadvantages.

SUMMARY

According to one embodiment of the present disclosure, a transdermal test sensor assembly adapted to determine an analyte concentration of a fluid sample is disclosed. The assembly comprises a sensor support including at least one reservoir adapted to hold a liquid. The assembly further comprises a test sensor being coupled to the sensor support. The test sensor forms at least one aperture therein. At least a portion of the at least one aperture is adjacent to the at least one reservoir. The assembly further comprises a hydrogel composition positioned on the test sensor. The hydrogel composition is linked to the at least one reservoir via the at least one aperture.

According to another embodiment of the present disclosure, a transdermal analyte-testing assembly adapted to determine an analyte concentration of a sample is disclosed. The assembly comprises a sensor support including at least one reservoir adapted to hold a liquid. The assembly further comprises a test sensor being coupled to the sensor support. The test sensor forms at least one aperture therein. At least a portion of the at least one aperture is adjacent to the at least one reservoir. The assembly further comprises a hydrogel composition being linked to the at least one reservoir via the at least one aperture. The assembly further comprises an analyte-testing instrument coupled to the sensor support. The analyte-testing instrument is adapted to determine an analyte concentration of a sample.

According to another embodiment of the present disclosure, a non-invasive method of determining a concentration of at least one analyte in a body fluid is disclosed. The method comprises the act of providing a transdermal test sensor assembly including a sensor support, a test sensor, and a hydrogel composition. The sensor support includes at least one reservoir. The at least one reservoir includes a liquid. The test sensor is coupled to the sensor support. The test sensor forms at least one aperture therein. At least a portion of the at least one aperture is adjacent to the at least one reservoir. The hydrogel composition is linked to the at least one reservoir via the at least one aperture. The method further comprises the act of contacting the transdermal sensor to an area of skin such that the hydrogel composition is positioned between the skin and the test sensor. The method further comprises coupling an analyte-testing instrument to the transdermal test sensor assembly. The method further comprises determining the concentration of the analyte using the analyte-testing instrument.

The above summary is not intended to represent each embodiment, or every aspect, of the present invention. Additional features and benefits of the present invention are apparent from the detailed description and figures set forth below.

BRIEF DESCRIPTION OF THE DRAWINGS

FIG. 1b is an exploded, perspective view of the test sensor assembly of FIG. 1a.

DESCRIPTION OF ILLUSTRATED EMBODIMENTS

The present invention is directed to a transdermal test sensor assembly adapted to assist in determining a concentration of at least one analyte. The transdermal test sensor assembly has hydrating features.

Transdermal test sensors contain a hydrogel composition, which may serve as an interface between the sensor and the skin. A hydrogel composition is defined herein as a cross-linked polymer gel. The hydrogel composition generally comprises at least one monomer and a solvent. The solvent is typically substantially biocompatible with the skin. Non-limiting examples of solvents that may be used in the hydrogel composition include water and a water mixture. The amount of solvent in the hydrogel is generally between about 10 to about 95 weight percent and may vary depending on the monomer amount, crosslinking, and/or the desired composition of the gel.

The transdermal test sensor assists in determining the concentration of the desired analyte by using the hydrogel as an osmotic agent to extract the analyte from a fluid such as ISF. Analytes that may be measured include glucose, lipid profiles (e.g., cholesterol, triglycerides, LDL, and HDL), fructose, lactate, and/or bilirubin. It is contemplated that other analyte concentrations may be determined. One non-limiting example of the transdermal sensor's use is to determine the glucose concentration in a user's ISF.

Figure 1A:
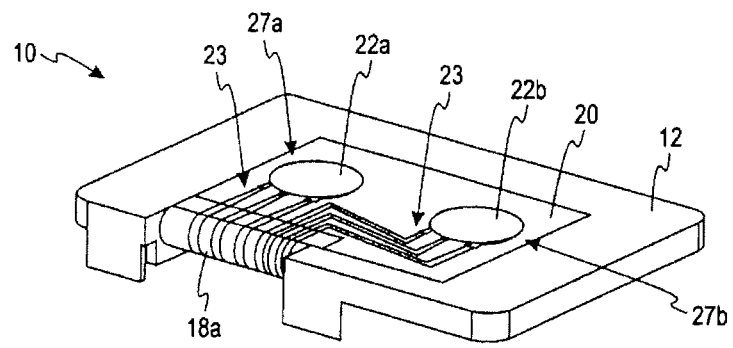
FIG. 1a is a perspective view of a test sensor assembly according to one embodiment of the present invention.

In the embodiment of FIGS. 1a,b, a transdermal test sensor assembly 10 is illustrated according to one embodiment of the present invention. Although in this embodiment, the test sensor is an electrochemical sensor, it is contemplated that the present invention may also be applied to other sensors (e.g., optical test sensors). An example of an electrochemical sensor includes a standard, three-electrode design utilizing a catalytic, platinum-containing working electrode, a counter electrode, and a reference electrode. It is contemplated that other electrochemical sensors may be used including those with fewer electrodes such as a two-electrode electrochemical sensor, which includes a counter electrode and a working electrode.

The test sensor assembly 10 includes a sensor support 12 and a test sensor 14. The test sensor 14 is positioned generally parallel and adjacent to the sensor support 12. The sensor support 12 of FIGS. 1a,b includes a recessed area 16 having dimensions generally similar to the dimensions of the test sensor 14. It is desirable for the recessed area 16 to have dimensions substantially similar to the dimensions of the test sensor 14 to inhibit movement of the test sensor 14 relative to the sensor support 12. It is contemplated that the test sensor assembly of the present invention may include a mechanism to further inhibit movement of the test sensor 14 relative to the sensor support 12. For example, the test sensor 14 of FIGS. 1a,b includes a flexible element 18a that may be adapted to attach to a corresponding curved element 18b of the sensor support 12. It is contemplated that other mechanisms suitable for inhibiting movement of the test sensor 14 with respect to the sensor support 12 may also be used. For example, an adhesive may be positioned between the sensor 14 and the sensor support 12. Alternatively, the sensor support 12 may include plastic molded pins extending from the recessed area 16 through corresponding holes in the test sensor 14. The pins may be, for example, heat-staked or sonic welded to maintain the sensor 14 in place.

An outwardly-facing surface 20 of the test sensor 14 includes a hydrogel composition 22a,b. Although in the illustrated embodiment, the hydrogel 22a,b is generally circular in shape, it is contemplated that the hydrogel 22a,b may be of any shape. Moreover, although two hydrogel compositions 22a,b are illustrated, it is contemplated that any number of hydrogel compositions 22a,b may be included on the surface 20 of test sensor 14. The hydrogel 22a,b generally has a thickness of from about 0.05 mm to about 5 mm and, more specifically, has a thickness of from about 0.01 mm to about 1 mm. The surface area of the test sensor 14 covered by the hydrogel 22a,b in one embodiment is from about 0.1 cm$^2$ to about 100 cm$^2$. The hydrogel 22a,b is generally positioned over a plurality of electrodes 23. The plurality of electrodes 23 includes a counter electrode, a reference electrode, and a working (measuring) electrode. It is contemplated that other electrode structures may be used.

Figure 1B:
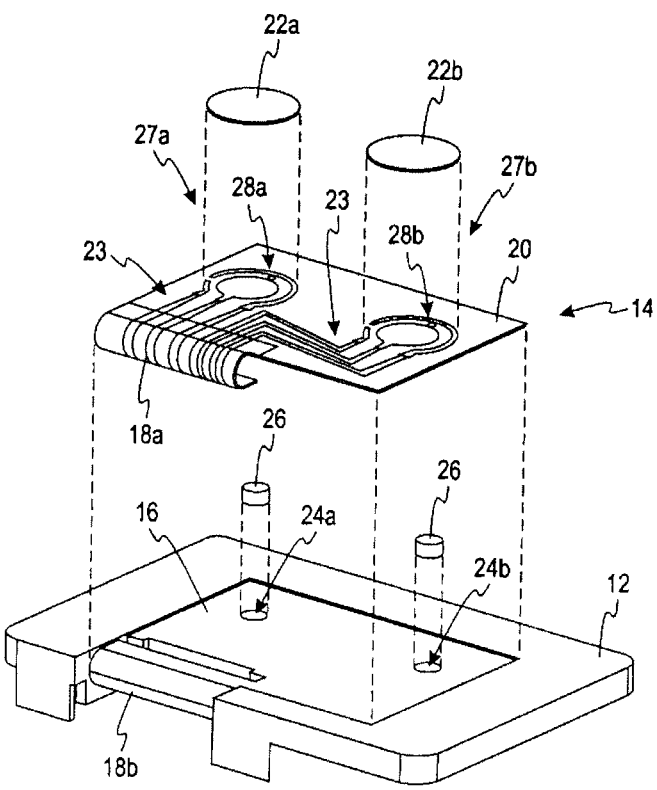

In the embodiments of FIGS. 1a,b and 2, the test sensor 14 is a dual-sensor test sensor, wherein each of two sensors 27a,b is independent of the other. The test sensor assembly 10 includes two corresponding reservoirs 24a,b (see FIG. 1b). It is contemplated that a different number of sensors 27 and corresponding reservoirs 24 may be used with the present invention.

The reservoirs 24a,b of the illustrated embodiment are located within the recessed area 16. The reservoirs 24a,b are adapted to store a liquid 26 for hydrating the hydrogel composition 22a,b. The types of liquid that may be stored in the reservoirs 24a,b include a second hydrogel, a solvent, or the like. The solvent may be the same as or different from the solvent used in the hydrogel composition 22a,b. Although in the illustrated embodiment of FIG. 1b, the reservoirs 24a,b have a generally round shape, it is contemplated that the reservoirs 24a,b may have other shapes.

The test sensor 14 includes at least one aperture 28a,b per sensor 27a,b formed therein that is positioned generally below the hydrogel 22a,b and generally above the reservoir 24a,b, as shown in FIGS. 1a,b. The at least one aperture 28a,b serves as a conduit for the liquid 26 and the hydrogel 22a,b. Thus, as the hydration of the hydrogel 22a,b begins to decrease, the liquid 26 in the reservoir 24a,b supplies additional hydration to the hydrogel 22a,b. It is desirable for the liquid 26 to generally include a greater percent of solvent than the hydrogel 22a,b so that the hydrogel 22a,b may more readily absorb the liquid 26. The hydrogel 22a,b may become saturated at a certain point at which it will no longer be able to absorb the liquid 26. By reducing or substantially eliminating dehydration of the hydrogel 22a,b, the transport properties of the hydrogel 22a,b are not altered, and more accurate testing results may be obtained.

Figure 2:
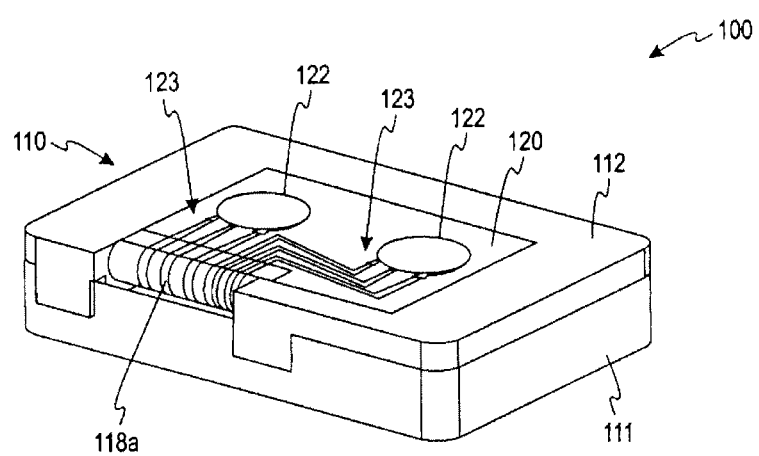
FIG. 2 is a perspective view of a test sensor assembly of the present invention being coupled to an analyte-testing instrument.

The test sensor assembly of the present invention may be coupled to an analyte-testing instrument, or meter, as shown in the embodiment of FIG. 2. Referring to FIG. 2, a meter assembly 100 includes a test sensor assembly 110 coupled to a meter 111. The test sensor assembly 110 of FIG. 2 is substantially similar to the test sensor assembly 10 of FIGS. 1a,b and described above. In the illustrated embodiment, the meter 111 is coupled to a surface of a sensor support 112 opposite a test sensor 114. It is contemplated that the meter 111 may be coupled to other portions of the test sensor assembly 110. It is contemplated that any mechanism suitable for maintaining the test sensor assembly 110 and the meter 111 in a substantially fixed position may be used including, but not limited to, snaps, screws, or other fasteners. The meter 111 is adapted to determine the concentration of the desired analyte in a fluid sample such as an ISF sample.

To test an analyte (e.g., glucose) concentration in an ISF sample, a hydrogel composition 128a,b on the test sensor 114 is placed against a user's skin, thereby coupling the skin and the test sensor 114. The test sensor assembly 110 may be applied at a skin site such as the volar forearm between the wrist and elbow such that the hydrogel 122a,b is positioned generally between the skin site and the test sensor 114. It is contemplated that the test sensor assembly 110 may be applied at other skin sites such as the abdomen. It is contemplated that the meter 111 and/or the test sensor assembly 110 may be used for continual glucose monitoring or for non-continual glucose monitoring.

It may be desirable for the skin to be pre-treated to increase the skin permeability prior to applying the test sensor assembly 110. One example of pre-treating is to use ultrasound energy to disrupt the lipid bilayer of the stratum corneum so as to increase the skin permeability. By increasing the skin permeability, the amount of ISF used in transdermal sampling is increased. This results in improved sampling of the analytes of interest found in the ISF.

One non-limiting source of an ultrasound energy system is Sontra SonoPrep® ultrasonic skin permeation system marketed by Sontra Medical Corporation (Franklin, Mass.). The SonoPrep® system applies relatively low frequency ultrasonic energy to the skin for a limited duration (from about 10 to 20 seconds). The ultrasonic horn contained in the device vibrates at about 55,000 times per second (55 KHz) and applies energy to the skin through the liquid-coupling medium to create cavitation bubbles that expand and contract in the coupling medium.

Referring again to FIG. 2, according to one method, the meter assembly 100 is used for continual, transdermal monitoring of an analyte (e.g., glucose). In a continual monitoring system, the meter assembly 100 measures an analyte concentration (e.g., glucose) at regular intervals, which may range from milliseconds to minutes. Because the meter 100 may remain coupled to the sensor support 112 for extended periods of time, it is desirable that the meter 113 be of a compact size to minimize the bulkiness and inconvenience to a user. The meter 100 may also be adapted to wirelessly transmit testing data to, for example, a remote computer data management system 130.

As discussed above, the hydrogel generally includes a monomer(s) and a solvent. In addition to a monomer and solvent, it is contemplated that the hydrogel composition may include other materials. For example, an electrolyte may be added to the hydrogel composition. The electrolyte desirably contains a high salt concentration that assists in exerting osmotic pressure on the skin. By exerting osmotic pressure on the skin, the electrolyte assists in driving out the ISF that contains the analyte. Non-limiting examples of electrolytes that may be used include sodium and potassium salts of chloride, phosphate, citrate, acetate, and lactate.

The hydrogel composition may further include a liquid. The liquid may include electrolytes. The concentration of electrolytes in the liquid is generally high enough to ensure the functionality of the process of determining an analyte concentration, yet low enough that the liquid remains hypotonic relative to the body fluid being tested (e.g., ISF). The electrolytes may cause a diffusional driving force of numerous solutes into the hypotonic liquid. The driving force may also enhance the transport of analyte (e.g., glucose) toward the sensor surface. Alternatively or additionally, the liquid may include a composition for generally increasing the efficiency of reactions involved in the process of determining the analyte concentration. For example, the liquid may include a buffer having a pH level conducive for the glucose oxidase conversion of glucose in the hydrogel.

The hydrogel composition may further include an enzyme to assist in determining the analyte concentration. Depending on the analyte, an enzyme may assist in converting the analyte into a species amenable to detection, such as electrochemical detection. One example of an enzyme that may be used in determining glucose is glucose oxidase. It is contemplated that other enzymes may be used, such as glucose dehydrogenase. If other analytes are of interest, an appropriately selected enzyme may assist in determining the concentration of that analyte.

The hydrogel composition may further include a permeation enhancer. Permeation enhancers are desirable in applications in which the hydrogel composition is applied to the skin. The permeation enhancer assists in opening up pores of the skin. Non-limiting examples of permeation enhancers that may be used include, but are not limited to, squalene, unsaturated fatty acids, glycerol derivatives of fatty alcohols, dimethylsulfoxide, and alkyl esters of fatty acids.

Other materials that may be added to the hydrogel composition include, but are not limited to, biocides, humectants, surfactants, and combinations thereof. Biocides assist in exhibiting bacterial growth. Non-limiting examples of biocides that may be used include the Paraben series of preservatives, sodium benzoate, benzalkonium chloride, and trialkyl amines. Humectants assist in applications in which it is desirable to keep the skin moist. Non-limiting examples of humectants that may be used include glycerol, hexylene glycol and sorbitol, maltitol, polydextrose, propylene glycol, lactic acid, and lactate metal salts. Surfactants assist in coupling the hydrogel composition with the skin to obtain an improved contact therebetween. Non-limiting examples of surfactants that may be used include alkyl phenols such as TRITON® X-100 (octyl phenol ethoxylate having a molecular formula of $C_{14}H_{22}O(C_2H_4O)_n$, in which an average "n" is 9 or 10), and sorbitol and sorbitol derivatives such as the TWEEN™ series.

The hydrogel composition desirably possesses sufficient mechanical and thermal stability to provide a relatively static, reactive, and aqueous conduit between the dermal sampling site and the sensor. More specifically, it is desirable for the hydrogel composition to have physical uniformity and flexibility, and mechanical stability against shear force. It is also desirable for the hydrogel composition to maintain the porosity of the skin. The hydrogel composition also desirably displays a relatively high degree of compressibility to assist in securing good skin/sensor connectivity or skin adhesiveness.

It is also desirable for the hydrogel composition to have porosity large enough for enzyme entrapment. For example, in some applications involving the determination of glucose concentration, it is desirable for the hydrogel composition to provide a matrix for glucose oxidase and a diffusion passage for glucose and hydrogen peroxide.

A hydrogel that may be used with the present invention may comprise a first monomer, a second monomer, a cross-linking agent, and a solvent. The first monomer is selected from the group consisting of N-vinyl pyrrolidone, hydroxy alkyl methacrylates, acrylamide, and N,N di-alkyl acrylamides. The second monomer is selected from the group consisting of alkyl (meth)acrylates, N-vinyl acylamide, vinyl esters, and vinyl ethers. The ratio of the first monomer to the second monomer is from about 0.1:99.9 to about 99.9:0.1.

One example of a hydrogel that may be used comprises N-vinyl pyrrolidone as a first monomer and vinyl acetate as a second monomer. The hydrogel further comprises a photoinitiator (2-Hydroxy-4'-(2-hydroxyethoxy)-2-methylpropiophenone) marketed as Irgacure® 2959 by Ciba Specialty Chemicals Pty Ltd., and a cross-linking agent (diethylene glycol divinyl ether). The copolymeric mixture includes 50 parts N-vinyl pyrrolidone, 50 parts vinyl acetate, 0.5 parts Irgacure® 2959, and 0.5 parts diethylene glycol divinyl ether.

Alternative Embodiment A

A transdermal test sensor assembly adapted to determine an analyte concentration of a fluid sample, the test sensor assembly comprising:

a sensor support including at least one reservoir adapted to hold a liquid;

a test sensor being coupled to the sensor support, the test sensor forming at least one aperture therein, at least a portion of the at least one aperture being adjacent to the at least one reservoir; and a hydrogel composition positioned on the test sensor, the hydrogel composition being linked to the at least one reservoir via the at least one aperture.

Alternative Embodiment B

The assembly of Alternative Embodiment A, wherein the at least one reservoir further includes a liquid.

Alternative Embodiment C

The assembly of Alternative Embodiment B, wherein the hydrogel includes a solvent, the liquid of the at least one reservoir includes a solvent, the solvent percentage of the liquid being greater than the solvent percentage of the hydrogel.

Alternative Embodiment D

The assembly of Alternative Embodiment A, wherein the sensor support further includes a recessed area having dimensions generally similar to dimensions of the test sensor, the recessed area being adjacent to the test sensor, the at least one reservoir being positioned within the recessed area.

Alternative Embodiment E

The assembly of Alternative Embodiment A, wherein the assembly further comprises a coupling mechanism for coupling the test sensor assembly to an analyte-testing instrument.

Alternative Embodiment F

The assembly of Alternative Embodiment A, wherein the hydrogel composition comprises at least one monomer and a solvent.

Alternative Embodiment G

A transdermal analyte-testing assembly adapted to determine an analyte concentration of a sample, the analyte-testing assembly comprising:

a sensor support including at least one reservoir adapted to hold a liquid;

a test sensor being coupled to the sensor support, the test sensor forming at least one aperture therein, at least a portion of the at least one aperture being adjacent to the at least one reservoir;

a hydrogel composition being linked to the at least one reservoir via the at least one aperture; and an analyte-testing instrument coupled to the sensor support, the analyte-testing instrument being adapted to determine an analyte concentration of a sample.

Alternative Embodiment H

The assembly of Alternative Embodiment G, wherein the at least one reservoir further includes a liquid.

Alternative Embodiment I

The assembly of Alternative Embodiment G, wherein the hydrogel includes a solvent, the liquid of the at least one reservoir includes a solvent, the solvent percentage of the liquid being greater than the solvent percentage of the hydrogel.

Alternative Embodiment J

The assembly of Alternative Embodiment G, wherein the sensor support further includes a recessed area having dimensions generally similar to dimensions of the test sensor, the recessed area being adjacent to the test sensor, the at least one reservoir being positioned within the recessed area.

Alternative Embodiment K

The assembly of Alternative Embodiment G, wherein the hydrogel composition comprises at least one monomer and a solvent.

Alternative Embodiment L

The assembly of Alternative Embodiment G, wherein the analyte-testing instrument is adapted to determine the analyte concentration at pre-selected time intervals.

Alternative Process M

A non-invasive method of determining a concentration of at least one analyte in a body fluid, the method comprising the acts of:

providing a transdermal test sensor assembly including a sensor support, a test sensor, and a hydrogel composition, the test sensor support including at least one reservoir, the at least one reservoir including a liquid, the test sensor being coupled to the sensor support, the test sensor forming at least one aperture therein, at least a portion of the at least one aperture being adjacent to the at least one reservoir, the hydrogel composition being linked to the at least one reservoir via the at least one aperture;

contacting the transdermal sensor to an area of skin such that the hydrogel composition is positioned between the skin and the test sensor;

coupling an analyte-testing instrument to the transdermal test sensor assembly; and determining the concentration of the analyte using the analyte-testing instrument.

Alternative Process N

The method of Alternative Process M, wherein the area of skin is pre-treated.

Alternative Process O

The method of Alternative Process M, wherein the act of determining the concentration of the analyte using the analyte-testing instrument is repeated at pre-selected time intervals.

Alternative Process P

The method of Alternative Process M, wherein the hydrogel includes a solvent, the liquid of the at least one reservoir includes a solvent, the solvent percentage of the liquid being greater than the solvent percentage of the hydrogel.

Alternative Process Q

The method of Alternative Process M, wherein the sensor support further includes a recessed area having dimensions generally similar to dimensions of the test sensor, the recessed area being adjacent to the test sensor, the at least one reservoir being positioned within the recessed area.

Alternative Process R

The method of Alternative Process M, wherein the hydrogel composition comprises at least one monomer and a solvent.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. A test sensor assembly for determining a concentration of an analyte in a fluid sample, the test sensor assembly comprising:

a sensor support including at least one reservoir configured to hold liquid;

a test sensor coupled to the sensor support, the test sensor forming at least one aperture therein, at least a portion of the at least one aperture being proximal to the at least one reservoir; and a hydrogel composition positioned on the test sensor, the hydrogel composition being linked to the at least one reservoir via the at least one aperture.

2. The test sensor assembly of claim 1, wherein the sensor support further includes a recessed area within which is seated the test sensor, the recessed area having dimensions similar to dimensions of the test sensor such that the recessed area inhibits movement of the test sensor relative to the sensor support.

3. The test sensor assembly of claim 1, wherein the test sensor includes a plurality of electrodes, the hydrogel composition being positioned over at least a portion of the plurality of electrodes.

4. The test sensor assembly of claim 1, further comprising a liquid in the at least one reservoir, wherein the liquid hydrates the hydrogel composition.

5. The test sensor assembly of claim 1, further comprising a liquid in the at least one reservoir, wherein the hydrogel composition includes a first percentage of a solvent, and the liquid includes a second percentage of a solvent, the second solvent percentage of the liquid being greater than the first solvent percentage of the hydrogel composition.

6. The test sensor assembly of claim 1, wherein the test sensor further comprises a flexible coupling mechanism coupling the test sensor to the sensor support.

7. The test sensor assembly of claim 1, wherein the sensor support is configured to mechanically couple to a meter and the test sensor is configured to electrically couple to the meter.

8. The test sensor assembly of claim 1, wherein the hydrogel composition comprises at least one monomer and a solvent.

9. A transdermal analyte-testing assembly for determining an analyte concentration in a sample, the transdermal analyte-testing assembly comprising:

a sensor support including at least one reservoir configured to hold liquid;

a test sensor coupled to the sensor support, the test sensor forming at least one aperture therein, at least a portion of the at least one aperture being proximal to the at least one reservoir;

a hydrogel composition fluidly coupled to the at least one reservoir via the at least one aperture; and an analyte-testing instrument coupled to the sensor support, the analyte-testing instrument being operable to determine the analyte concentration of the sample.

10. The transdermal analyte-testing assembly of claim 9, further comprising a liquid in the at least one reservoir, wherein the liquid hydrates the hydrogel composition through the at least one aperture.

11. The transdermal analyte-testing assembly of claim 9, further comprising a liquid in the at least one reservoir, wherein the hydrogel composition includes a first percentage of a solvent, and the liquid includes a second percentage of a solvent, the second solvent percentage of the liquid being greater than the first solvent percentage of the hydrogel composition.

12. The transdermal analyte-testing assembly of claim 9, wherein the sensor support further includes a recessed area having dimensions generally similar to dimensions of the test sensor, the recessed area being adjacent to the test sensor, the at least one reservoir being positioned within the recessed area.

13. The transdermal analyte-testing assembly of claim 9, wherein the hydrogel composition comprises at least one monomer and a solvent.

14. The transdermal analyte-testing assembly of claim 9, wherein the analyte-testing instrument is adapted to determine the analyte concentration at pre-selected time intervals.

15. A method of assembling a test sensor assembly for analyzing an analyte in a body fluid sample, the method comprising:

providing a sensor support with a reservoir configured to hold liquid;

positioning a liquid in the reservoir of the sensor support;

providing a test sensor with an aperture extending therethrough;

attaching the test sensor to the sensor support such that at least a portion of the aperture is proximal to the reservoir; and positioning a hydrogel composition on the test sensor such that the hydrogel composition is fluidly coupled to the liquid in the reservoir via the aperture.

16. The method of claim 15, wherein the sensor support further includes a recessed area within which is seated the test sensor, the recessed area having dimensions similar to dimensions of the test sensor such that the recessed area inhibits movement of the test sensor relative to the sensor support.

17. The method of claim 15, wherein the test sensor includes a plurality of electrodes, the hydrogel composition being positioned over at least a portion of the plurality of electrodes.

18. The method of claim 15, wherein the hydrogel composition includes a first percentage of a solvent, the liquid of the at least one reservoir includes a second percentage of a solvent, the second solvent percentage of the liquid being greater than the first solvent percentage of the hydrogel composition.

19. The method of claim 15, wherein the test sensor further comprises a flexible coupling mechanism attaching the test sensor to the sensor support.

20. The method of claim 15, wherein the hydrogel composition comprises at least one monomer and a solvent.

* * * * *